United States Patent
Mortara et al.

(10) Patent No.: US 11,147,465 B2
(45) Date of Patent: Oct. 19, 2021

(54) ABRASIVE ELECTRODE

(71) Applicant: Mortara Instrument, Inc., Milwaukee, WI (US)

(72) Inventors: Justin Mortara, Milwaukee, WI (US); Jeffrey Plate, Milwaukee, WI (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1113 days.

(21) Appl. No.: 15/146,624

(22) Filed: May 4, 2016

(65) Prior Publication Data

US 2016/0324473 A1   Nov. 10, 2016

Related U.S. Application Data

(60) Provisional application No. 62/157,281, filed on May 5, 2015.

(51) Int. Cl.
    *A61B 5/0408* (2006.01)
    *A61B 5/0402* (2006.01)
    *A61B 5/00* (2006.01)

(52) U.S. Cl.
    CPC ........ *A61B 5/04025* (2013.01); *A61B 5/0408* (2013.01); *A61B 5/6833* (2013.01); *A61B 2562/0217* (2017.08)

(58) Field of Classification Search
    CPC . A61B 5/04025; A61B 5/0408; A61B 5/0478; A61B 5/0488; A61B 5/0492
    See application file for complete search history.

(56) References Cited

U.S. PATENT DOCUMENTS

| | | |
|---|---|---|
| 2,621,657 A | 12/1952 | Leech |
| 4,027,664 A | 6/1977 | Heavner et al. |
| 4,029,086 A | 6/1977 | Corasanti |
| 4,155,354 A | 5/1979 | Rasmussen |
| 4,257,424 A | 3/1981 | Cartmell |
| 4,265,253 A | 5/1981 | Abraham |
| 4,270,544 A | 6/1981 | Gilden et al. |
| 4,274,419 A | 6/1981 | Tam et al. |
| 4,300,575 A | 11/1981 | Wilson |
| 4,311,152 A | 1/1982 | Modes et al. |
| 4,319,579 A | 3/1982 | Cartmell |
| 4,331,153 A | 5/1982 | Healy |
| 4,488,557 A | 12/1984 | Engel |
| 4,524,087 A | 6/1985 | Engel |
| 4,539,996 A | 9/1985 | Engel |
| 4,559,950 A | 12/1985 | Vaughan et al. |
| 4,595,013 A | 6/1986 | Jones et al. |
| 4,674,511 A | 6/1987 | Cartmell |
| 4,679,564 A | 7/1987 | Sessions |
| 4,700,710 A | 10/1987 | Hoffman |

(Continued)

FOREIGN PATENT DOCUMENTS

GB   2 240 928   8/1991

*Primary Examiner* — Lee S Cohen
(74) *Attorney, Agent, or Firm* — Lee & Hayes, P.C.

(57) ABSTRACT

An electrode includes an electrically conductive member having a first surface oriented to face the skin of a patient when the electrode is placed on the skin of the patient. The electrode further includes a housing member. The electrode further includes an abrasive member configured to abrade the skin of the patient. The electrode further includes an integrated gripping portion configured to allow an operator to grip the gripping portion by hand and abrade the skin by moving the electrode using the gripping portion.

16 Claims, 6 Drawing Sheets

(56) References Cited

U.S. PATENT DOCUMENTS

| | | |
|---|---|---|
| 4,706,680 A | 11/1987 | Keusch et al. |
| 4,738,263 A | 4/1988 | Seebach et al. |
| 4,757,817 A | 7/1988 | Healy |
| RE32,724 E | 8/1988 | Cartmell |
| 4,768,514 A | 9/1988 | De Marzo |
| 4,777,954 A | 10/1988 | Keusch et al. |
| 4,798,208 A | 1/1989 | Faasse, Jr. |
| 4,838,273 A | 6/1989 | Cartmell |
| 4,934,383 A | 6/1990 | Glumac |
| 5,114,424 A | 5/1992 | Hagen et al. |
| 5,305,746 A | 4/1994 | Fendrock |
| 5,309,909 A | 5/1994 | Gadsby et al. |
| 5,458,141 A | 10/1995 | Neil |
| 5,645,063 A | 7/1997 | Straka, Jr. |
| 6,690,959 B2 | 2/2004 | Thompson |
| 6,711,427 B1 | 3/2004 | Ketelhohn |
| 7,366,558 B2 | 4/2008 | Virtanen et al. |
| 8,406,843 B2 | 3/2013 | Tiegs et al. |
| 2014/0030647 A1 | 1/2014 | Moriyama et al. |
| 2014/0148869 A1 | 5/2014 | Stickney et al. |

FIG. 1

PRIOR ART

SECTION A-A

FIG. 15

ABRASIVE ELECTRODE

CROSS REFERENCE TO RELATED APPLICATIONS

The present application claims priority to and the benefit of U.S. Provisional Patent Application No. 62/157,281, titled "Abrasive Electrode," filed May 5, 2015, which is incorporated herein by reference in its entirety.

BACKGROUND

The present disclosure relates generally to electrodes for sensing biopotential events. In particular, the disclosure relates to an electrode that includes an abrasive surface for performing skin preparation in addition to sensing and recording biopotential events.

Motion artifacts are a problem during the measurement of biopotentials, particularly in long-term electrocardiogram (ECG) monitoring of coronary care patients and in exercise (stress) ECGs. Motion artifacts can be defined as motion induced fluctuation of the electrical potential across the skin of the patient. Motion artifacts manifest themselves as electrical interference which is often superimposed on the desired biopotential signal and minimizes the usefulness of the biopotential signal for diagnostic and clinical purposes. Motion artifacts are generally caused by the movement of the patient relative to the electrode applied to the patient's skin, thereby disturbing the skin potential and creating extraneous readouts on the ECG monitor which either mask or cause a shift in the baseline of the desired biopotential signal.

SUMMARY

One embodiment of the present disclosure relates to an electrode. The electrode includes an electrically conductive member having a first surface oriented to face the skin of a patient when the electrode is placed on the skin of the patient. The electrode further includes a housing member. The electrode further includes an abrasive member configured to abrade the skin of the patient. The electrode further includes an integrated gripping portion configured to allow an operator to grip the gripping portion by hand and abrade the skin by moving the electrode using the gripping portion.

DETAILED DESCRIPTION

Light abrasion of the skin reduces the electrical potential and minimizes the impedance of the skin of the patient, thereby reducing motion artifacts and improving signal or trace quality of the biopotential signal. Reliable signals or trace results from many electrodes are highly dependent on adequate skin preparation prior to application of the electrodes. Proper skin preparation is time consuming because typical stress electro-cardiograms usually require between three and 12 electrodes and typically use about 10 electrodes. Skin preparation is normally used to remove the epidermal layer of the skin of the patient and is carried out in a variety of ways. The most common method of preparing the skin is to rub the patient's skin with a gritty material contained in a carrier or to rub the patient's skin with a rough surfaced material to which an antiseptic such as alcohol or other solvent is applied. After briskly rubbing the skin, the skin is dried and again rubbed with a dry cloth. If, after the electrodes are applied, a proper signal or trace is not obtained from one or more of the electrodes, the malfunctioning electrodes must be identified and removed and the skin must be prepared again. The electrodes are then reapplied to the skin of the patient, and this procedure is repeated until an adequate and accurate signal is received from each electrode. The effectiveness of the skin preparation is highly dependent on the technique used as well as the level of skill of the person preparing the skin. Predictably, the effectiveness of the skin preparation in this uncontrolled manner is highly variable between electrode locations as well as between patients.

According to some embodiments, the present disclosure is directed to an electrode device having an integrated abrading portion as well as a portion configured to allow a user (e.g., technician) to abrade the skin without utilizing a separate tool, such as an applicator gun. The electrode may be used to perform skin preparation after application of the electrode to the desired location on the skin of the patient and before the recording of biopotential events. In some embodiments, the electrode may include a rotatable conductive portion as well as a rotatable penetration portion for abrasion of the epidermal layer of skin. Both the conductive portion and penetration portion may be rotated after application of the electrode to the skin of the patient to prepare the skin and thereby minimize motion artifacts arising from skin potential variations and skin impedance. In some embodiments, the electrode is pre-gelled and disposable, although non pre-gelled and reusable electrodes are within the scope of the present disclosure as well.

In some embodiments, the conductive portion of the electrode retains the epidermal penetrating portion therein and is provided with an electrolyte such as a gel material in a recess formed between the conductive portion and penetrating portion. The conductive portion may be secured for rotational movement relative to an adhesive coated sheet member which is used to adhere the electrode to the skin. When the electrode is pre-gelled, it may be provided with a removable cover for protecting the adhesive coated sheet member and the penetrating portion having the electrolyte gel therein. In some embodiments, the conductive portion is a carbon based, silver plated center member, and the penetrating portion is a flexible screen-type member.

Some embodiments of the present disclosure may provide a surface mounted medical electrode capable of a more uniform and consistent skin preparation between individual electrodes and patients.

Some embodiments of the present disclosure may provide an electrode which reduces or minimizes the interference of motion artifacts and skin impedance with biopotential signals.

Some embodiments of the present disclosure may provide a surface mounted medical electrode having a rotatable abrasive member for abrading the skin after application of the electrode to the patient.

Some embodiments of the present disclosure may provide a surface mounted electrode that reduces or eliminates technique variability in skin preparation, thereby reducing or minimizing motion artifact while decreasing the likelihood that the skin of the patient will be abraded excessively.

Some embodiments of the present disclosure may provide an electrode which forms a gel column between the circumferential housing, the electrically conductive center member and the skin of the patient to maintain electrical contact between the skin of the patient and the center member during use of the electrode as well as reducing the time necessary for application of an electrode to a patient.

Some embodiments of the present disclosure may provide a surface mounted electrode which is inexpensive to manufacture and easy to assemble.

Some embodiments of the present disclosure may provide a system to abrasively prepare the skin, which is contained entirely on the electrode (e.g., a disc which is attached to the free rotating abrasive pad).

Some embodiments of the present disclosure may provide a system to abrade the skin and sense and measure biopotentials that may allow for abrasion without the use of an applicator gun (e.g., may allow abrasion through use of a hand tool portion of the system).

FIGS. 1-4 illustrate a surface mounted electrode and applicator gun 70, such as that set forth in U.S. Pat. No. 5,458,141, which is commonly owned by the assignee of the present invention and is incorporated herein as if fully set forth below. The electrode shown in FIGS. 1-4 generally consists of a circular sheet member 10 having an annular cutout portion 12 in the center thereof into which a collar 14 is inserted. The collar 14 is shaped to hold an electrically conductive member 16 therein. A ring member 18 is further employed to clamp around the upper portion of the collar 14. The sheet member 10 is coated on one side with a skin adhesive layer 20. The adhesive is protected during storage with a protective cover 22. A spongy abrasive member 24 (see FIG. 2) is provided with an electrolyte gel thereon and is placed in contact with the conductive member 16. The abrasive member 24 is protected during storage with the protective cover 26.

Figure 1:
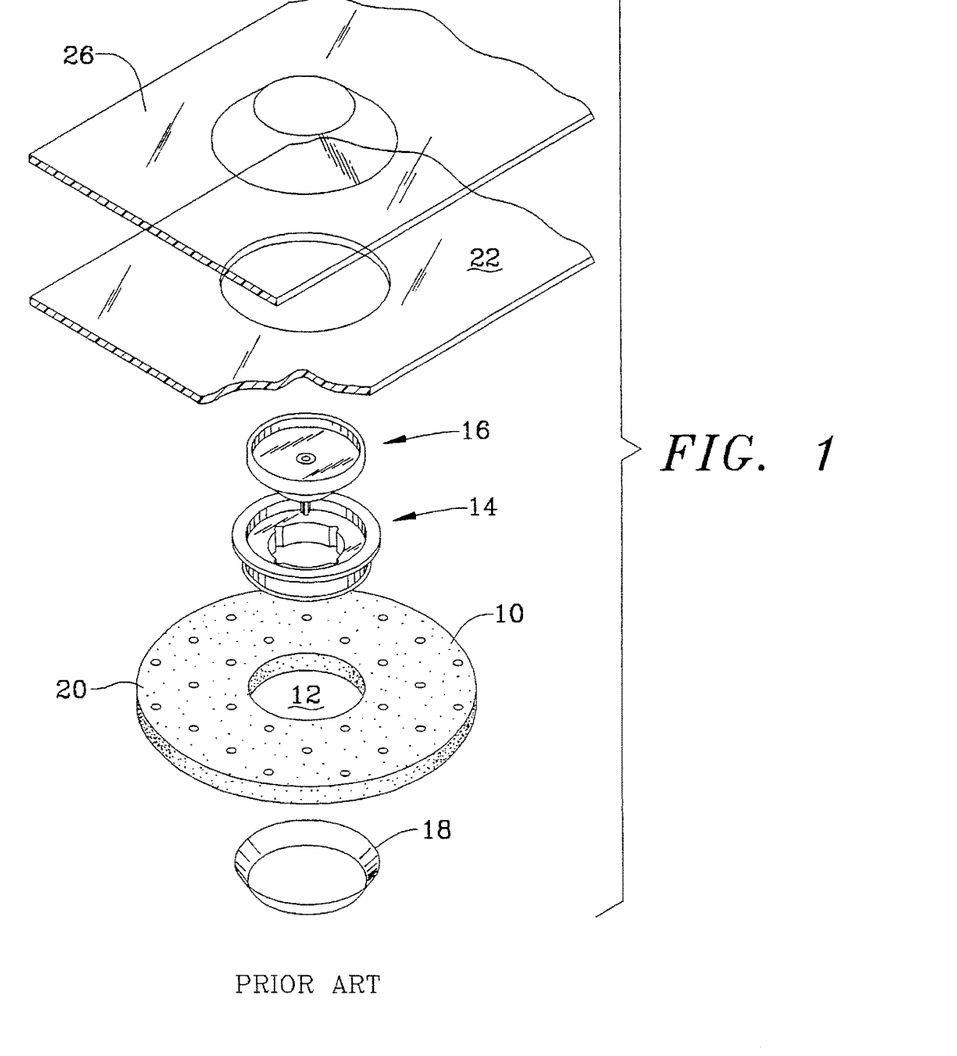
FIG. 1 is an exploded view of a surface mounted medical electrode, illustrating the components which make up the electrode except for the abrasive electrolyte-containing member.

The collar 14 has the general configuration of an inverted hat having a flat base 28 and a vertical wall 30 normal and integral with the flat base 28 terminating in a contoured flange 32. The flat base 28 has an annular opening 34 in the center thereof with a diameter less than the diameter of the inner wall 30. Around the annular opening 34, is a vertical wall 36 having slots 38 cut therein about every 90 degrees. The walls 30 and 36 extend above the plane of the base 28 leaving a channel 40 therebetween. The collar 14 is generally molded from a semi-flexible, nonconductive plastic material such as an acetate-based material, nylon, polyester, polyethylene or polypropylene. The wall 36 is made sufficiently thin so that it can be flexed under pressure. The diameter of the collar 14 is substantially greater than its height. The inner periphery of the wall 36 is provided with a ridge 42 which functions to retain the conductive member therein.

Figure 2A:
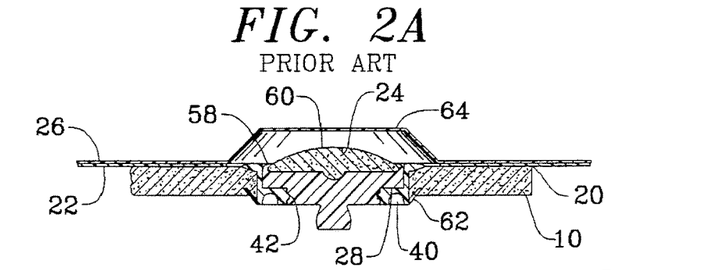
FIGS. 2A and 2B are cross-sectional views of the electrode of FIG. 1.
Figure 2B:
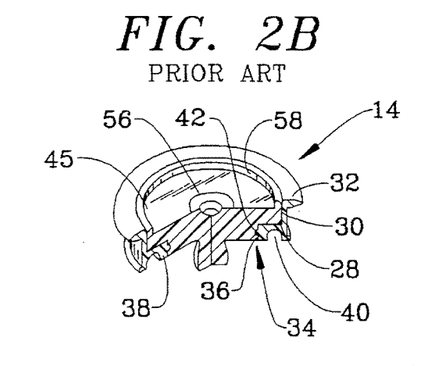
Figure 3:
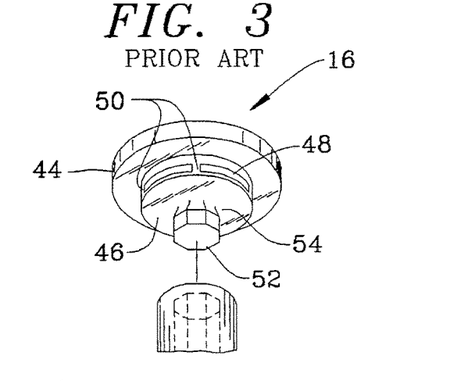
FIG. 3 is a perspective view of the projecting stud of the prior art conductive member and the coupler of the applicator gun illustrating the manner in which the applicator gun is connected to the stud of the prior art electrode of FIG. 1 for rotation of the conductive member by the applicator gun.

The electrically conductive member 16 is adapted to be snapped into the collar 14. The electrically conductive member 16 may be manufactured from a synthetic resin impregnated with carbon from a suitable electrically conductive metal or metal containing material or other suitable electrically conductive material. As shown in FIGS. 2 and 3, the electrically conductive member 16 includes a lower portion 44 having a textured convex lower surface 45 and a thickness substantially equal to the depth of the cup formed by the flange 32, wall 30 and base 28 of the collar. Integral with the lower portion 44 is an upper portion 46 of reduced diameter relative to the lower portion. The upper portion 46 has a diameter equal to that of the annular opening 34 in the collar 14. The circumference of the upper portion has a slot 48 therein which is interrupted by detents 50 positioned normal to the slot 48. The slot 48 of the conductive member 16 receives the ridge 42 in the wall 36 of the collar 14 to prevent the conductive member from moving vertically within the collar. The detents 50 of the conductive member 16 engage in the slots 38 in the flexible wall 36 of the collar 14 to prevent the conductive member from being rotated except by the predetermined torque/force of the applicator gun 70. A downwardly extending stud 52 provided on the bottom of the conductive member 16 preferably includes a polygonal outer surface 54 so that the coupler of the applicator gun can be drivingly secured over the stud to rotate the conductive member 16.

Figure 4:
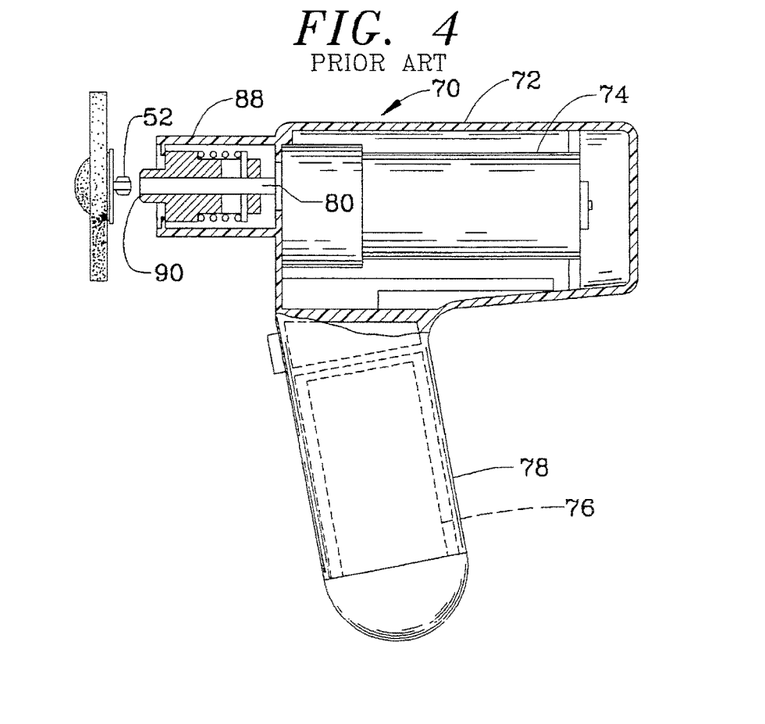
FIG. 4 is a schematic view of an applicator gun used to drive the movable conductive element and abrasive member of the electrode of FIG. 1 and an electrode of the present disclosure to perform skin preparation.

The penetrating portion for abrading or penetrating the epidermal layer of skin is a separate porous abrasive member 24 as illustrated in FIGS. 2A and 4. The abrasive member 24 is a generally fibrous pad incorporating abrasive fibers and having a convexly curved surface 60 and a diameter substantially the same as the diameter of the lower portion 44 of the conductive member 16. A flange 58 is folded against the edges of the abrasive member 24 to clamp the abrasive member 24 in the conductive member 16. The abrasive member 24 is loaded with electrolyte gel so that when the electrode is applied to the skin, the electrolyte gel provides electrical contact between the skin and the conductive member 16.

The assembled collar 14, conductive member 16 and abrasive member 24 are snapped together and placed in the annular opening 12 of the adhesive coated sheet member 10. The adhesive coating 20 contacts the upper surface of the flange 32 of the collar 14 to secure the collar 14 in place relative to the sheet member. A snap ring 18 as shown in FIG. 1 is snapped over the wall 30 of the collar. The snap ring 18 is held in place by a ridge 62 extending around the outer terminating edge of the wall 30 of the collar 14.

FIGS. 3 and 4 generally illustrate the applicator gun 70 which can be coupled to an electrode and used to abrade the skin. The applicator gun 70 generally includes a housing 72 within which is mounted an electric motor 74 driven by AC or DC current from a suitable current source. The motor illustrated is driven by a rechargeable battery 76 held in place in a quickly disconnectable case 78 which also serves as the handle of the applicator. The lower end of the case includes recessed electrical contacts for battery recharging. The motor has a shaft 80 to which a coupler 88 is attached. The coupler 88 includes a polygonal recess 90 thereon which is shaped to receive the specifically shaped stud 52 of the electrode therein.

Figure 5:
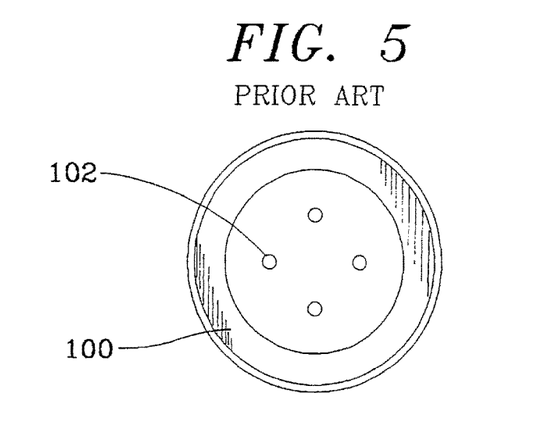
FIG. 5 is a perspective view, partially in cross section, showing a further electrode.
Figure 6:
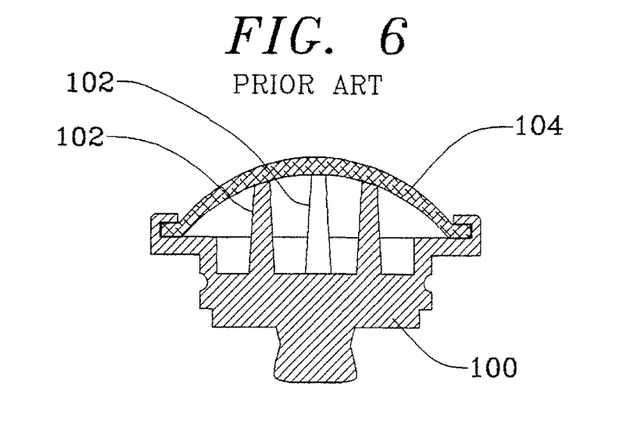
FIG. 6 is an elevated view of the electrode of FIG. 5 illustrating the mesh screen and gel removed therefrom.

FIGS. 5 and 6 are illustrative of a further variation of an electrode according to an exemplary embodiment. For the sake of brevity, like numbers have been added to like members described above with respect to the electrode shown in FIGS. 1-4. In this electrode, the conductor member 100 is modified to include four equally spaced apart post members 102 extending therefrom. The conductor member 100 of this electrode includes a silver chloride paint sprayed thereon to increase the electrical conductivity between the patient, electrolyte gel and conductor member 100. The post members 102 in this electrode provide rigid support for the mesh screen 104 which replaces the abrasive member 24 of the electrode described above. In this electrode the electrolyte gel (not shown) is positioned between the conduction member 100 and the mesh screen 104. In operation, the post members 102 rigidly support the mesh screen 104 to prevent the flexing of the mesh screen 104 as the skin of the patient is prepared. Additionally, the rigid support of the mesh screen 104 by the post members 102 inhibits the flow of the electrolyte gel (not shown) during use.

FIGS. 7-12 are illustrative of another electrode 110 according to an exemplary embodiment. The electrode 110 may include a radiolucent member that generally includes an electrically conductive center member 112 received in a circumferential housing 114. The housing 114 includes a flexible screen member 116 received therein on the side of the housing 114 opposite to the center member 112. As with the electrodes described above, the electrode 100 further includes an adhesive coated sheet member 118 surrounding a retaining ring 150. The sheet member 118 may be formed of a cross linked polyethylene foam having an adhesive thereon to facilitate the attachment of the electrode 100 to the skin of the patient. Prior to use, the adhesive surface of the sheet member 118 is protected by a paper-like protective cover 120, and the surface of the electrode is further protected in a tray-like package (not shown) or by a further protective cover 121.

Figure 7:
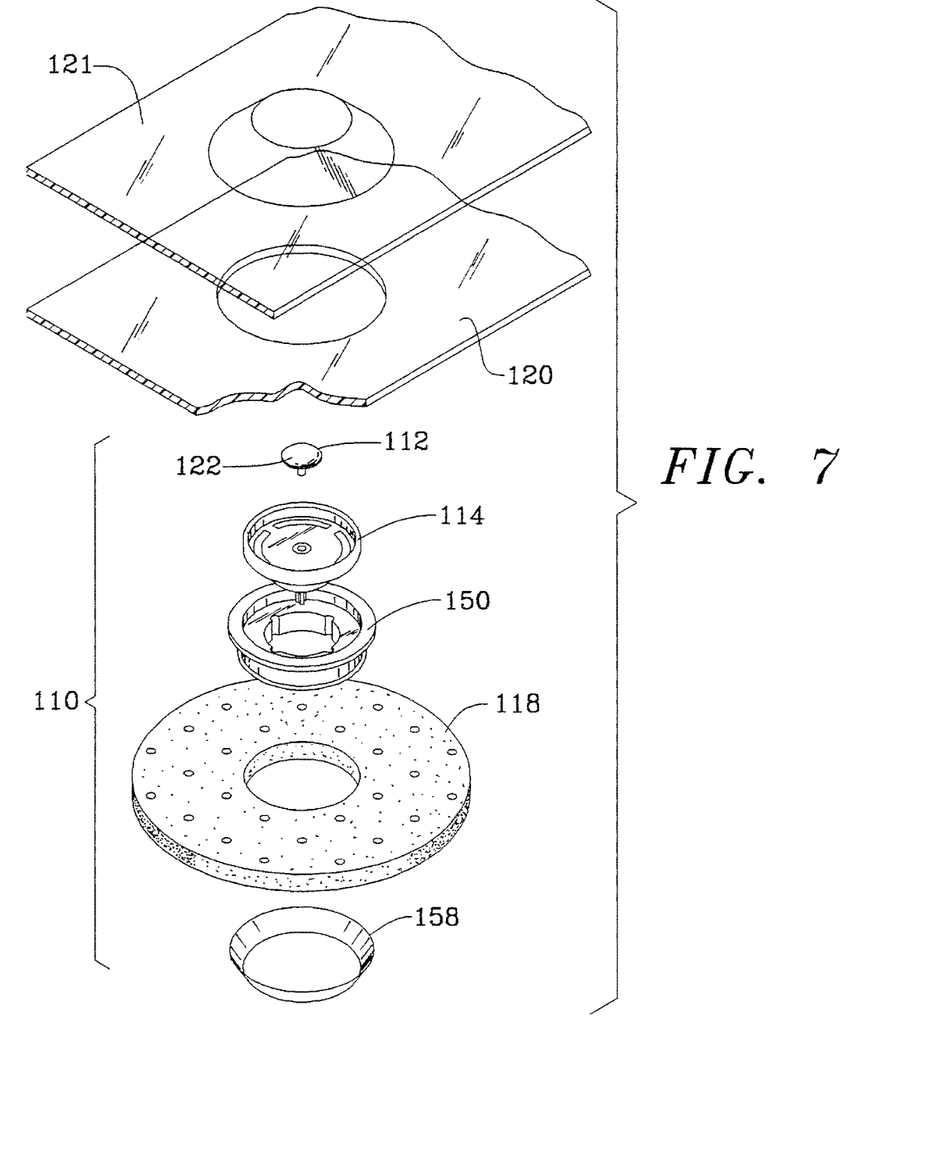
FIG. 7 is an exploded perspective view of an electrode according to an exemplary embodiment.
Figure 10:
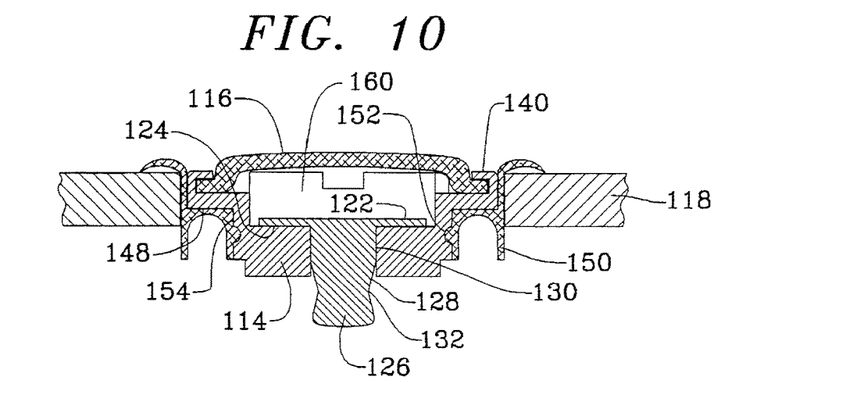
FIG. 10 is a cross sectional view of the electrode shown in FIG. 8 taken generally along lines 10-10 of FIG. 8.

In some embodiments, the center member 112 is a plastic carbon member having a thin silver plated layer thereon which has been treated with silver chloride to enhance ion flow therethrough as well as to form a low impedance point of connection with the wires (not shown) of the electrode. As shown in FIGS. 7 and 10, the center member 112 includes a generally flat first surface 122 with a circularly shaped outer circumference having a diameter which is greater than the diameter of the aperture 134 in the housing 114 as described below. The second surface 124 of the center member 112 includes the post member 126 extending therefrom. The post member 126 includes tapered surface 128 which extends from the second surface 124 of the center member 112. The tapered surface 128 includes a slight rib 130 thereon and decreases in circumference to form a snap area 132 on the post member 126 which is contacted and engaged by a snap type of electrode connector (not shown). The rib 130 is shaped to frictionally contact a portion of the housing 114 described below. In some embodiments, the post member 126 is not hexagonally or otherwise particularly shaped to receive reciprocal motion from the applicator gun 70 (FIG. 4) thereon.

Figure 9:
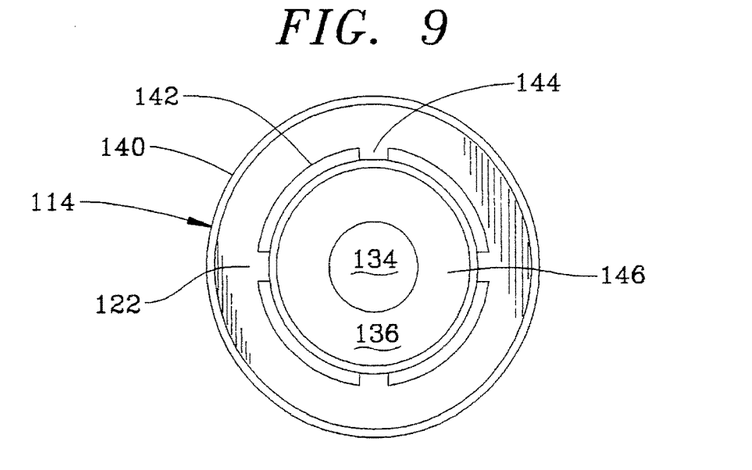
FIG. 9 is an elevated view of the electrode as illustrated in FIG. 8 with the mesh screen removed.
Figure 11:
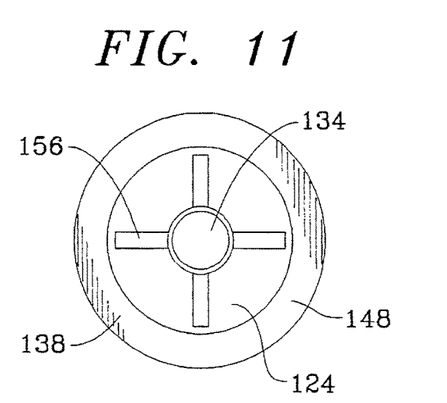
FIG. 11 is an elevated view of the electrode illustrated in FIGS. 7-10 showing the post member and second surface of the housing.

The circumferential housing 114 may be formed of a rigid plastic or similar material, in some embodiments. As shown in FIGS. 9-11, the housing 114 includes an aperture 134 extending therethrough and first and second surfaces 136 and 138 respectively. The aperture 134 is formed to frictionally receive the center member 112 therein. The first surface 136 of the housing 114 is best shown in FIG. 9. The first surface 136 includes an outer circumferential rib 140 which forms the outer periphery of the housing 114 and an inwardly positioned annular ring shaped surface 142 having a plurality of channels 144 formed therein. During assembly, the circumferential rib 140 is crimped or otherwise formed to retain the screen member 116 thereon as shown in FIG. 10. A recessed area 146 is also located inwardly of the annular surface 142 to surround the aperture 134 and receive the first and second surfaces 122 and 124 of the center member 112 therein.

The second surface 138 of the housing 114 is best shown in FIGS. 7 and 11. The second surface 138 includes a generally flat contact surface 148 which is shaped to receive a portion of the retaining ring 150 thereagainst in a manner similar to the contact between the collar 14 and the conductive member 16 as shown in FIG. 2. The sidewall surface 154 of the housing 114 extends outwardly from the contact surface 148 and includes a circumferential recess 152 therein. The circumferential recess 152 is sized to frictionally receive a portion of the retaining ring 150 therein while allowing the housing to rotate with respect to the retaining ring 150. A plurality of radially extending ridge members 156 extend between the aperture 134 in the housing 114 and sidewall surface 154 of the housing 114 to enable the coupler 88 of the applicator gun 70 to contact the ridge members 156 and impart rotational movement to the housing 114. As with the collar 14 shown in FIG. 2, the retaining ring 150 of the present invention extends between the outer surface of the housing 114 and the sheet member 118 to retain the housing 114, center member 112 and screen member 116 in the sheet member 118 while allowing rotational movement between the housing 114 and retaining ring 150. Additionally, the snap ring 158 is positioned between the outer surface of the retaining ring 150 and the sheet member 118 to prevent rotational movement between the sheet member 118 and the retaining ring 150.

The screen member 116 may be constructed of a flexible silicon carbide or other abrasive material. The screen member 116 is sized so that when the outer circumference of the screen member 116 is positioned generally inwardly from and adjacent to the crimped outer circumferential rib 140, the screen member 116 contacts the annular ring surface 142 of the housing 114 and is bowed slightly outwardly therefrom, in some embodiments. This orientation is particularly useful to provide consistent abrasion of the skin of the patient because if the user of the applicator gun presses too hard during the preparation of the skin of the patient, the screen member 116 will flex to decrease the abrasion of the skin. This is in contrast to the electrode shown in FIGS. 5 and 6 wherein the mesh screen 104 is rigidly held in place by the post members 106.

The flexibility of the screen member 116 and the orientation of the screen member 116 with respect to the housing 114 and center member 112 are also useful during the use of the electrode. The electrolyte gel (not shown) is placed in the housing 114 to fill the space between the first surface 136 of the housing 114, the first surface 122 of the center member 112 and the screen member 116. When the electrode is applied to the skin of the patient, the sheet member 118 encircles the periphery of the housing 114 such that the electrolyte gel is trapped therein. During certain procedures such as ECG stress tests, the patient is exercising or otherwise moving around. This movement causes the skin which is in contact with the various electrodes to stretch or contract according to the movements of the patient. During this movement, the skin may press against or move away from the prior art electrode shown in FIGS. 5 and 6 because of the rigid support provided to the mesh screen 104 by the post members 106. This movement between the electrode and the skin of the patient causes muscle artifact and may even break the signal between the patient and the recording device. During use of the electrode, in some embodiments, the electrolyte gel forms a gel column in the electrode which responds to the movement of the skin of the patient to ensure that the electrolyte gel maintains electrical contact between the skin of the patient and the center member 112. The area between the circumferential rib 140 and the annular surface 142 on the first surface 136 of the housing 114 functions basically as a reservoir area 160 for the electrolyte gel in the present invention. For example, if the skin of the patient presses against the slightly flexed or raised center of the mesh screen, the electrolyte gel is pushed back into the recess of the housing and is forced to flow to the outer periphery of the housing 114 through the channels 144 in the annular surface 142 to the reservoir area 160 of the housing 114 between the circumferential rib 140 and the annular surface 142. When the skin of the patient draws away from the electrode, the electrolyte gel is drawn from the reservoir area 160 of the housing 114 through the channels 144 and into the recessed area 146 to ensure that a continuous column of electrolyte gel extends between the skin of the patient and the center member 112.

Figure 12:
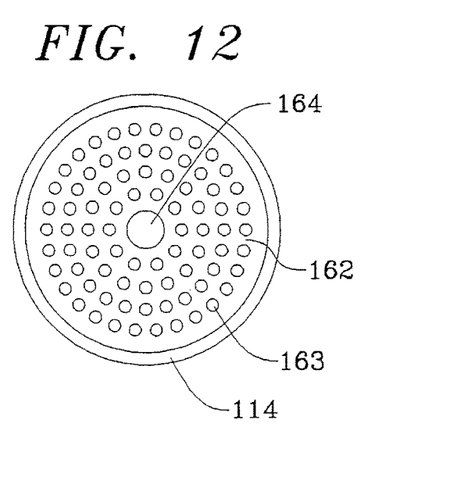
FIG. 12 is an elevated view of another electrode according to an exemplary embodiment.

FIG. 12 is illustrative of a further embodiment of the present disclosure wherein the screen member 116 of FIGS. 7-11 is replaced with a flexible member 162 having a plurality of spaced apart holes 163 extending therethrough that are generally larger than the openings in the screen member 116, and that also includes a centrally located and larger center hole 164. The electrode of this embodiment operates generally in the same manner as described with respect to FIGS. 7-11. Like numbers have been added to like members, and the features common to each embodiment are not separately repeated herein.

In the embodiments described above, an applicator gun or separate tool is generally used to rotate or otherwise manipulate the electrode to provide abrasion of the skin. In some embodiments, the electrode device may include a portion configured to be manipulated by hand, without the use of a separate tool such as an applicator gun.

Figure 13:
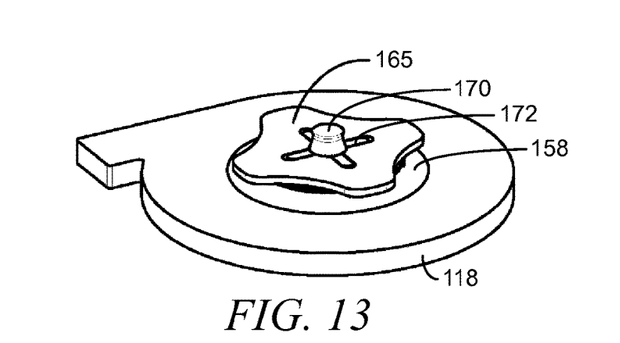
FIG. 13 is a perspective view of another electrode according to an exemplary embodiment.
Figure 14:
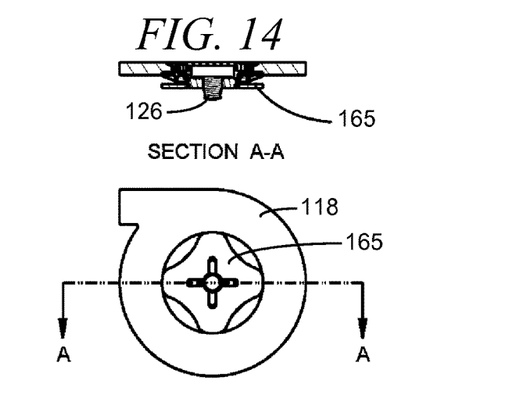
FIG. 14 is a cross-section view of the electrode of FIG. 13.
Figure 15:
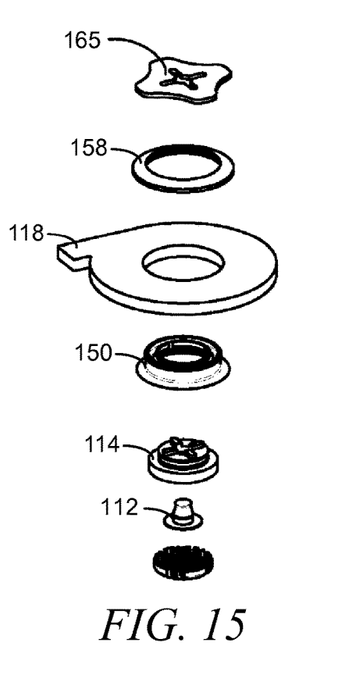
FIG. 15 is an exploded view of the electrode of FIG. 13.

FIGS. 13-15 are illustrative of an embodiment in which an electrode device includes a portion for use in moving the abrasive portion to abrade the skin without a separate tool. In various embodiments, various features described above may be utilized in conjunction with an electrode device similar to that shown in FIGS. 13-15 (e.g., a gel reservoir area for dispensing gel, contacts for connecting the electrode to an external monitor or other device, flexible abrasive materials, etc.). Similar elements described above that are shown in FIGS. 13-15 utilize similar reference numerals for ease of reference.

Figure 8:
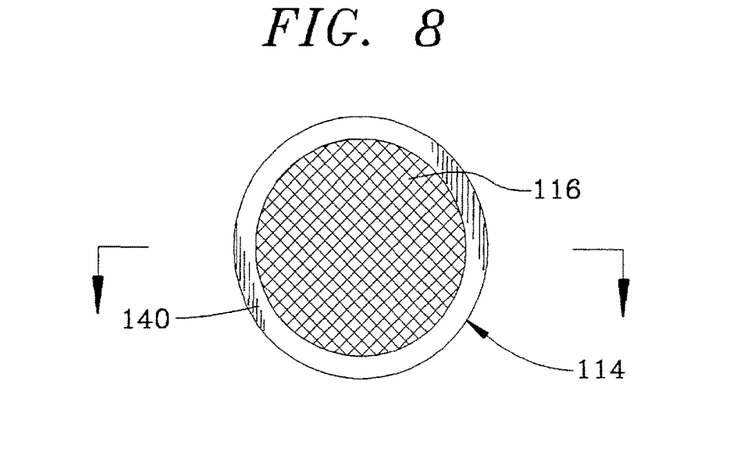
FIG. 8 is an elevated view of the assembled electrode shown in FIG. 7.

In some embodiments, as shown in FIG. 8 for example, the electrode device includes a moving screen member 116 (e.g., the abrasive pad). The screen member 116 is retained in position via a circumferential rib 140 (as shown in, for example, FIG. 10) or by any other type of shape formed on the first surface 122. An integrated gripping portion, such as a disc 165, is affixed to a housing 114 and permits an operator to rotate screen member 116 by hand without the use of additional tools or equipment (e.g., without the applicator gun 70).

Referring now to FIGS. 13-15, instead of a moving screen member 116, the disc 165 is shown affixed to a sheet member 118 via a connector 170 of any shape or size. As described above, center member 112 includes post member 126 extending therefrom. Connector 170 may affix to post member 126 of center member 112, locking disc 165 in place on top of snap ring 158. Snap ring 158 is positioned between disc 165 and sheet member 118 to prevent rotational movement between the sheet member 118 and the retaining ring 150.

Connector 170 may be of any shape or size and couples disc 165 to the rest of the electrode device to allow rotation of disc 165 by a user to rotate sheet member 116. Further, connector 170 may affix disc 165 to the rest of the assembly of electrode 110 in other ways, in some embodiments.

Disc 165 may be any shape or size. For example, disc 165 is shown with a roughly rectangular shape, with concave edges. This may allow for the rotation of disc 165 manually, such as by a user placing his or her fingers within the concave portions of disc 165 and rotating the electrode device to abrade the skin. In some embodiments, disc 165 or another portion of the electrode device may be formed with a structure configured to allow for abrasion to be performed via hand or via a tool. For example, disc 165 may include a recess, protrusion, or other feature configured to allow for mating with applicator gun 70 to optionally utilize applicator gun 70 for abrasion in addition to hand-applied abrasion. Disc 165 is shown to include a slot 172 through which a connection between screen member 116 and connector 170 is formed. Slot 172 may further be used to rotate disc 165 in order to rotate screen member 116 (either manually or using a tool that can be inserted into the slot).

In some embodiments, the gripping portion may be configured to have a relatively low profile to reduce an overall height or thickness of the electrode device. For example, in some embodiments, the gripping portion may be designed to be only a portion of the thickness of the assembled electrode device (e.g., one half, one third, one quarter, one fifth, etc.). In some embodiments, the hand tool may be no wider than a width of sheet member 118 (or screen member 116 in the embodiment of FIG. 8).

In various embodiments, the gripping portion may be any other type of tool that can be used to grip the electrode device by hand to abrade the skin. The gripping portion may include any type of shape, such as circular, oval, rectangular, square, etc. In some embodiments, the gripping portion may include a handle or other elongated portion extending upwards axially from the sheet member 118 and/or other portions of the electrode device. In some embodiments, the gripping portion may include a friction surface against which a user may place a hand and rotate the electrode device through friction between the hand and the friction surface. In various other embodiments, various other features configured to allow a user to manipulate the electrode by hand and abrade the skin without use of a separate tool may be utilized, and all such modifications are contemplated within the scope of the present disclosure.

Referring to FIG. 14, a top view and cross-section view of the electrode 110 is shown. The edges of disc 165 are shown protruding from the rest of the electrode assembly, allowing a user to grip disc 165 in order to rotate the disc 165 and, therefore, the sheet member 116. The rest of the assembly may be substantially similar to the embodiment shown in FIG. 10.

Referring to FIG. 15, an exploded view of electrode 110 is shown, including disc 165 and housing 114.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.). By way of example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. An electrode comprising:
   an electrically conductive member having a first surface oriented to face the skin of a patient when the electrode is placed on the skin of the patient;
   a housing member configured to house the electrically conductive member;
   an abrasive member coupled to the housing member and structured to abrade the skin of the patient; and
   an integrated gripping portion coupled to at least one of the electrically conductive member, the housing member, or the abrasive member and configured to allow an operator to grip the gripping portion by hand and abrade the skin by using the gripping portion;
   wherein the gripping portion comprises a flat disc configured to be fixed in a substantially parallel configuration to the abrasive member when assembled.

2. The electrode of claim 1, wherein the gripping portion is configured to allow an operator to abrade the skin without using a tool external to the electrode.

3. The electrode of claim 1, wherein the gripping portion comprises at least one of one or more protrusions or one or more recesses configured for gripping by a hand of the operator.

4. The electrode of claim 3, wherein the gripping portion comprises a plurality of recesses configured to receive fingers of the operator for gripping the electrode to abrade the skin.

5. The electrode of claim 1, wherein the electrode further comprises a gel in contact with the conductive member, and wherein the electrode is a disposable pre-gelled medical electrode configured to reduce motion artifacts.

6. The electrode of claim 1, wherein the electrically conductive member further comprises an opposing stud on a second surface thereof for connection to an external monitor.

7. The electrode of claim 1, wherein the housing comprises an electrically nonconductive housing retaining the conductive member therein, the housing including an annular opening receiving the conductive member therein.

8. The electrode of claim 1, wherein the abrasive member is operatively retained by the housing and includes a gel in contact with the conductive member, wherein the abrasive member is movable relative to the conductive member, and wherein the abrasive member and the housing further form a gel reservoir area therebetween such that when the abrasive member is pressed against the skin of the patient the gel is pushed by the skin into the reservoir area.

9. The electrode of claim 8, further comprising a sheet member operatively associated with the housing and having an adhesive material thereon to secure the electrode to the skin of the patient while allowing the abrasive member to be movable with respect to the skin of the patient and the sheet member.

10. The electrode of claim 9, wherein the reservoir area is oriented with respect to the abrasive member and the housing such that the gel flows from the reservoir area as the skin of the patient moves away from the abrasive member.

11. The electrode of claim 9, wherein the abrasive member is spaced apart from the conductive member and the gel is positioned between the abrasive member and the conductive member in a first position of the abrasive member, and wherein at least a portion of the gel is located between the skin of the patient and the abrasive member in a second position of the abrasive member.

12. The electrode of claim 9, wherein the abrasive member is oriented with respect to the housing to flex in response to contact with the skin of the patient.

13. The electrode of claim 9, wherein the electrode is an electrocardiogram electrode.

14. An electrode comprising:
   an electrically conductive member having a first surface oriented to face the skin of a patient when the electrode is placed on the skin of the patient;
   a housing member configured to house the electrically conductive member;
   an abrasive member coupled to the housing member and structured to abrade the skin of the patient; and
   an integrated gripping portion coupled to at least one of the electrically conductive member, the housing member, or the abrasive member, the integrated gripping portion comprising a plurality of recesses to receive fingers of an operator and configured to allow the operator to grip the gripping portion by hand and abrade the skin using the gripping portion without using a tool external to the electrode;
   wherein the gripping portion comprises a flat disc configured to be fixed in a substantially parallel configuration to the abrasive member when assembled.

15. The electrode of claim 14, wherein a width of the gripping member is less than a width of abrasive member.

16. The electrode of claim 14, wherein the gripping portion comprises a friction surface structured to create friction with a hand of the operator during rotation of the gripping portion.

* * * * *